United States Patent
Hernke

(10) Patent No.: US 11,017,898 B2
(45) Date of Patent: May 25, 2021

(54) PATIENT MONITOR SENSOR TYPE AUTO CONFIGURATION

(71) Applicant: General Electric Company, Schenectady, NY (US)

(72) Inventor: David George Hernke, Milwaukee, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1142 days.

(21) Appl. No.: 14/065,910

(22) Filed: Oct. 29, 2013

(65) Prior Publication Data
US 2015/0120249 A1   Apr. 30, 2015

(51) Int. Cl.
*G16H 40/63* (2018.01)
*A61B 5/0205* (2006.01)

(52) U.S. Cl.
CPC ........... *G16H 40/63* (2018.01); *A61B 5/0205* (2013.01); *A61B 2562/08* (2013.01)

(58) Field of Classification Search
CPC ..... A61B 5/0261; A61B 5/00; A61B 5/14551; A61B 1/3704; G01M 13/028; G16H 40/40; G05B 19/0426; G06F 19/3418; G01D 21/00
USPC .................. 600/310, 513, 322, 301; 128/897
See application file for complete search history.

(56) References Cited

U.S. PATENT DOCUMENTS

| | | | |
|---|---|---|---|
| 4,695,955 A * | 9/1987 | Faisandier | A61B 5/00 128/897 |
| 7,206,602 B1 | 4/2007 | Conway | |
| 7,787,952 B2 | 8/2010 | Brodnick et al. | |
| 2003/0034998 A1* | 2/2003 | Kodosky | G05B 19/0426 715/736 |
| 2003/0040881 A1* | 2/2003 | Steger | G16H 40/40 702/123 |
| 2003/0050545 A1* | 3/2003 | Hicks | A61B 5/14551 600/322 |
| 2005/0060202 A1* | 3/2005 | Taylor | G06F 19/3418 705/2 |
| 2005/0113704 A1 | 5/2005 | Lawson et al. | |
| 2008/0009682 A1 | 1/2008 | Hernke | |

(Continued)

OTHER PUBLICATIONS

Cypress USB 101: An Introduction to Universal Serial Bus 2.0, pp. 1-57 (Year: 2014).*

(Continued)

*Primary Examiner* — Regis J Betsch
*Assistant Examiner* — Kaleria Knox
(74) *Attorney, Agent, or Firm* — Andrus Intellectual Property Law, LLP

(57) ABSTRACT

A method and system that allows various sensor types to be connected to common input ports of a patient monitor. The system includes a data acquisition module that identifies the type of sensor connected to each one of a plurality of input ports. Once the sensor type has been identified, the data acquisition module configures amplification circuits and input circuits such that the output signal from the sensor is properly received and amplified within the patient monitor. The properly amplified output signal from the sensor, along with a sensor identifier, is supplied to a controller of the patient monitor. In this manner, the patient monitor can identify the type of sensor connected to each input port and properly display the conditioned output signal from the sensor.

15 Claims, 4 Drawing Sheets

(56) References Cited

U.S. PATENT DOCUMENTS

| | | | | |
|---|---|---|---|---|
| 2010/0113898 A1* | 5/2010 | Kim | ............... | A61B 5/0261 |
| | | | | 600/310 |
| 2010/0249540 A1* | 9/2010 | Lisogurski | ........... | A61B 5/0002 |
| | | | | 600/301 |
| 2011/0022748 A1 | 1/2011 | Edwards et al. | | |
| 2012/0004515 A1* | 1/2012 | Cao | ............... | A61N 1/3704 |
| | | | | 600/301 |
| 2014/0285225 A1* | 9/2014 | Cho | ............... | G01D 21/00 |
| | | | | 324/705 |

OTHER PUBLICATIONS

Search Report and Written Opinion from Corresponding PCT Application No. PCT/US2014/051199 dated Oct. 20, 2014, 10 pages.

Life Scope vs Bedside Monitors BSM-3000 series, Nihon Kohden, www.nihonkohden.com.

"Signal Conditioning Wheatstone Resistive Bridge Sensors", Texas Instruments, Application Report SLOA034—Sep. 1999, pp. 1-5.

"Thermistors in Single Supply Temperature Sensing Circuits", Microchip Technology Inc., DS00685B, 1999, pp. 1-13.

Second Office Action and Supplementary Search issued in connection with corresponding CN Application No. 201480059904.X dated Oct. 16, 2018 (English Translation not available) 10 pages.

* cited by examiner

PATIENT MONITOR SENSOR TYPE AUTO CONFIGURATION

BACKGROUND

The present disclosure generally relates to the field of patient monitoring. More specifically, the present disclosure relates to a patient monitor that includes one or more multi-function input ports that allow more than one type of sensor to be connected to each of the input ports.

Patient monitoring systems may incorporate a wide range of modality medical processes that are available to examine a patient's condition and health. Patient monitoring systems are able to receive various different types of physiological data obtained from sensors connected to a patient. Patient monitors can be configured to receive and analyze various different types of physiological data from a patient, such as pulse oximetry ($SpO_2$), cardiac output (CO), temperature, invasive blood pressure, non-invasive blood pressure (NIBP), oxygen saturation, as well as other physiological parameters. The type of sensors used with the patient depends upon the patient's physical condition and the reasons for monitoring the patient's health.

Based upon the large number of different inputs that can be received by the patient monitor, patient monitors typically include separate input ports specifically designed to receive a certain type of sensor. As an example, pulse oximetry sensors are optical based sensors that provide a standard type of output signal that must be conditioned and amplified within the patient monitoring device. Conversely, other sensors, such as temperature sensors, include a thermistor that changes resistance based upon temperature. A temperature sensor typically receives a drive signal from the patient monitor and the output signal received by the patient monitor provides an indication of the temperature of the patient.

Since modern patient monitors can be used with a relatively large number of different types of sensors, the input panel to the patient monitor often includes a significant number of separate, specifically designed input ports. Since each of the input ports includes its own hardware interface circuit, the interface circuit hardware and separate input ports can increase both the cost and complexity of the patient monitor.

SUMMARY

The present disclosure relates to a method and system that allows different types of sensors to be connected to the same input port of a patient monitor. The system and method of the present disclosure includes circuits and components that allow a data acquisition module of the patient monitor to determine the type of sensor connected to the input port and, based upon the identified sensor type, configure the input port and signal conditioning circuitry to properly handle the sensor data.

The data acquisition module is designed for use with a patient monitor that receives and monitors physiological data obtained from one or more sensors connected to the patient. Various different types of physiological data can be obtained from the patient, such as but not limited to pressure, temperature and the cardiac output of the patient. The data acquisition module includes at least one multi-mode input port. Each of the multi-mode input ports can receive one of the plurality of different sensor types. When the sensor is received within the input port, the sensor can deliver and receive signals from the data acquisition module.

The data acquisition module further includes an interface circuit that is coupled to the input port. The interface circuit is operable to selectively apply a default signal to the sensor when the sensor is initially connected to the input port. The interface circuit can include an adjustable voltage supply that initially applies the default signal to the sensor.

After the default signal is applied to the sensor, a processor positioned within the data acquisition module receives an output signal from the sensor. Based upon the received output signal, which is generated after application of the default signal, the processor can determine the type of sensor connected to the input port. Based upon the determined type of sensor, the processor generates a sensor identifier that is delivered to the patient monitor along with the conditioned output signal from the sensor.

The data acquisition module can further include a detection module that includes a plurality of amplifiers. When the data acquisition module determines the type of sensor connected to the input port, the detection module is configured to route the output signal from the sensor to one of a plurality of amplifiers to create an amplified output signal. The type of amplifier selected is based upon the type of sensor connected to the input port.

The interface circuit further includes an adjustable power supply that can be configured to apply both the default signal and a drive signal to each of the sensors. The processor of the data acquisition module selects the proper value for the drive signal based upon the determined type of sensor. In this manner, the data acquisition module is able to provide the required drive signal to each of the individual sensors.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

Figure 1:
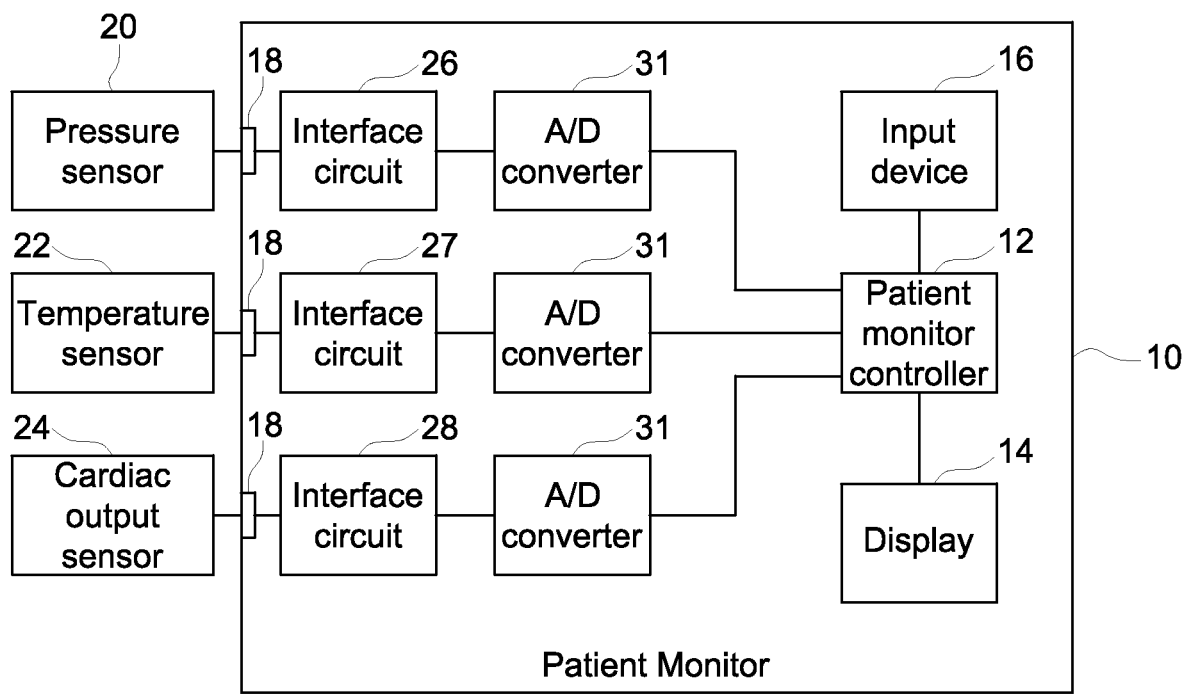
FIG. 1 is a schematic illustration of a prior art patient monitor that includes separate hardware interface circuits for various different types of sensors.

FIG. 1 illustrates a prior art patient monitor illustrating the complexity and cost associated with receiving physiological data from a large number of separate, individual sensors. As shown in FIG. 1, the patient monitor 10 includes a patient monitor controller 12 that operates the patient monitor display 14 and receives user input through an input device 16. The input device can be one of many different types, including a keyboard, touch pad or a touch screen incorporated into the display 14. The input device 16 allows a user to adjust various operating parameters of the patient monitor 10 and also to control the display 14.

The patient monitor 10 includes a plurality of input ports 18 that are each configured to receive a specific type of sensor. Typically, the input ports 18 are labeled on the patient monitor with the type of sensor that should be connected to the input port. In the embodiment shown in FIG. 1, the input ports 18 are shown connected to a pressure sensor 20, a temperature sensor 22 and a cardiac output sensor 24. Since each of these three sensors 20, 22 and 24 is a different type of sensor and provides a different output signal, the patient monitor 10 shown in FIG. 1 includes three separate interface circuits 26, 27 and 28. As an illustrative example, the pressure sensor 20 typically takes the form of a resistive bridge transducer that is driven by a voltage input and generates a differential voltage output across a pair of resistors formed as part of a wheatstone bridge. The interface circuit 26 is designed to supply the proper drive voltage to the pressure sensor 20 while also receiving the differential voltage signal from the pressure sensor.

Temperature sensor 22 is typically a thermistor that is formed as part of a voltage divider. Once again, the interface circuit 27 is specifically configured to provide the required drive signal to the temperature sensor 22 and to receive the voltage output from the temperature sensor 22, which is measured relative to ground potential.

The cardiac output sensor 24 is similar to the temperature sensor 22 and includes a variable resistor. The interface circuit 28 is specifically designed to provide a drive voltage to the cardiac output sensor 24 while receiving the voltage signal output from the cardiac output sensor, which is measured relative to ground potential. Since each of the three sensors 20, 22 and 24 require a different drive signal and generate a different type of output signal, the three interface circuits 26, 27 and 28 are included in the patient monitor and are specifically designed based upon the desired type of sensor connected to the respective input port 18.

In the embodiment illustrated in FIG. 1, each of the interface circuits 26, 27 and 28 provides the conditioned output signal from the sensor to an analog to digital converter 31. Although three separate A/D converters 31 are shown in FIG. 1, the A/D converters could be combined and each receive an output signal from one of the interface circuits 26, 27 or 28.

The digitized output signal from the A/D converter 31 is provided to the patient monitor controller 12. Since each of the input ports 18 receives a different type of sensor, the patient monitor controller 12 is able to condition the digitized output signal and provide the correct value for the physiological signal monitored from the patient.

As can be understood in FIG. 1, the patient monitor 10 required separate interface circuitry for each of the individual sensors connected to the patient monitor. Although this type of system provides the correct type of digitized data to the patient monitor controller 12, the inclusion of the multiple interface circuit increases both the cost and complexity of the patient monitor.

Figure 2:
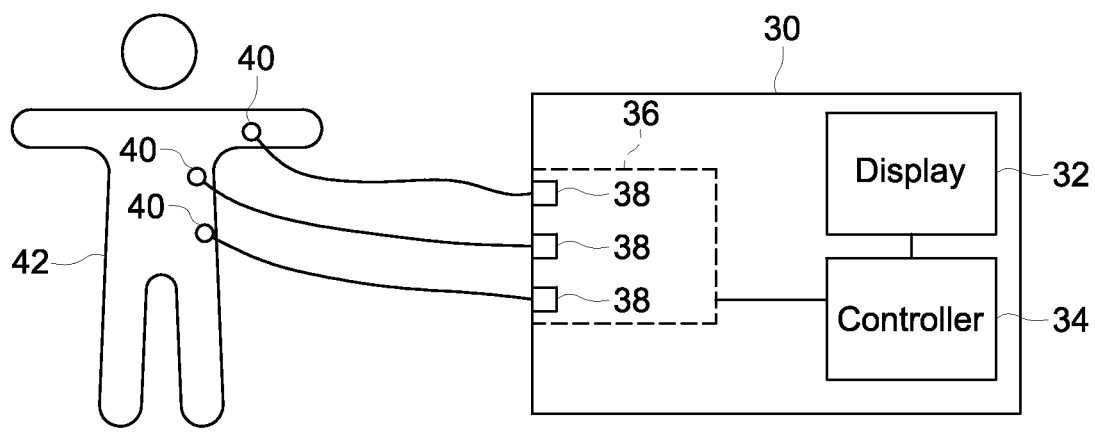
FIG. 2 is a schematic illustration illustrating the patient monitor including a data acquisition module that allows various types of sensor to be connected to the input ports of the data acquisition module.

FIG. 2 illustrates a patient monitor 30 constructed in accordance with the present disclosure. The patient monitor 30 includes a display 32 driven by the patient monitoring controller 34. The patient monitor 30 includes a data acquisition module 36 that includes a plurality of multi-mode input ports 38. The multi-mode input ports 38 are configured to allow any one of a plurality of different types of sensors to be connected to the input ports 38 of the data acquisition module 36. The data acquisition module 36 functions to initially identify the type of sensor connected to the input port 38 and, based upon the identified type of sensor, provides the required drive signal to the sensors. In addition, the data acquisition module 36 provides a sensor identifier along with a digitized output signal to the controller 34 such that the controller 34 can drive the display 32. In the embodiment shown in FIG. 2, three different types of sensors 40 are positioned in contact with the patient 42 being monitored.

Figure 3:
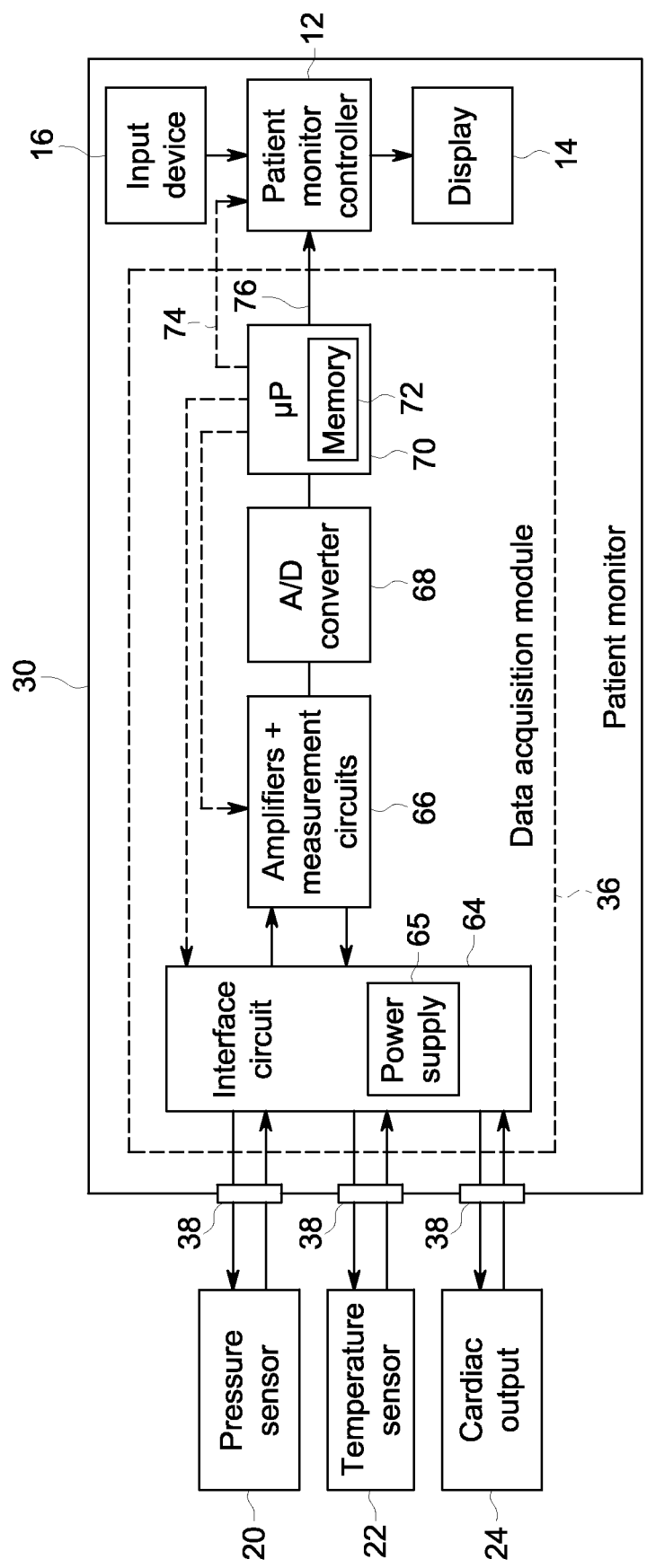
FIG. 3 is a schematic illustration of the operating components of the data acquisition module incorporated into the patient monitor.

FIG. 3 illustrates the patient monitor 30 including the data acquisition module 36 shown in greater detail. As illustrated in FIG. 3, the data acquisition module 36 includes three multi-mode input ports 38 that each can be connected to one of a series of individual sensors. In the embodiment shown in FIG. 3, pressure sensor 20 is connected to the first input port 38, a temperature sensor 22 is connected to the second input port while a cardiac output sensor 24 is connected to the third input port 38. Although three different types of sensors are shown in the embodiment of FIG. 3, it should be understood that various other types of sensors could be utilized or less than three sensors utilized while operating within the scope of the present disclosure.

Figure 4:
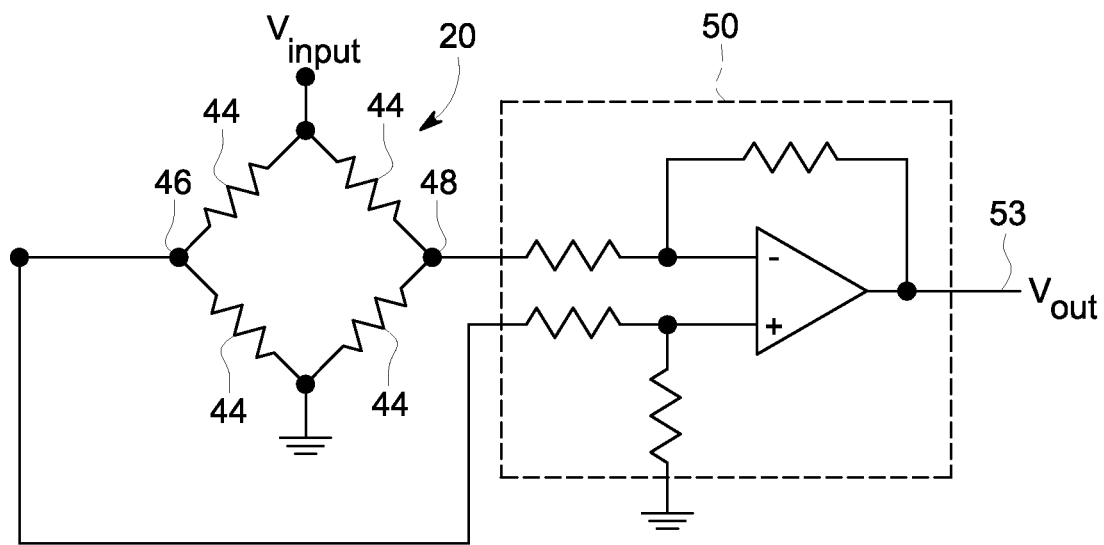
FIG. 4 is a circuit schematic showing the signal conditioning from a differential pressure sensor.

Although various different types of pressure sensors 20 can be utilized with the patient monitor, one example of a resistive bridge pressure sensor 20 is shown in FIG. 4. In the embodiment shown in FIG. 4, the pressure sensor 20 includes a resistive bridge network including four separate resistors 44, at least two of which change in value depending upon the pressure exerted on the resistors. A drive voltage ($V_{input}$) is supplied to the resistive bridge and a differential voltage is measured between points 46 and 48. The differential voltage between points 46 and 48 is thus an indication of the pressure measured by the pressure sensor 20. In the embodiment shown in FIG. 4, the differential voltage is applied to an amplifier 50 that generates an amplified output signal ($V_{out}$) at line 53.

Figure 5:
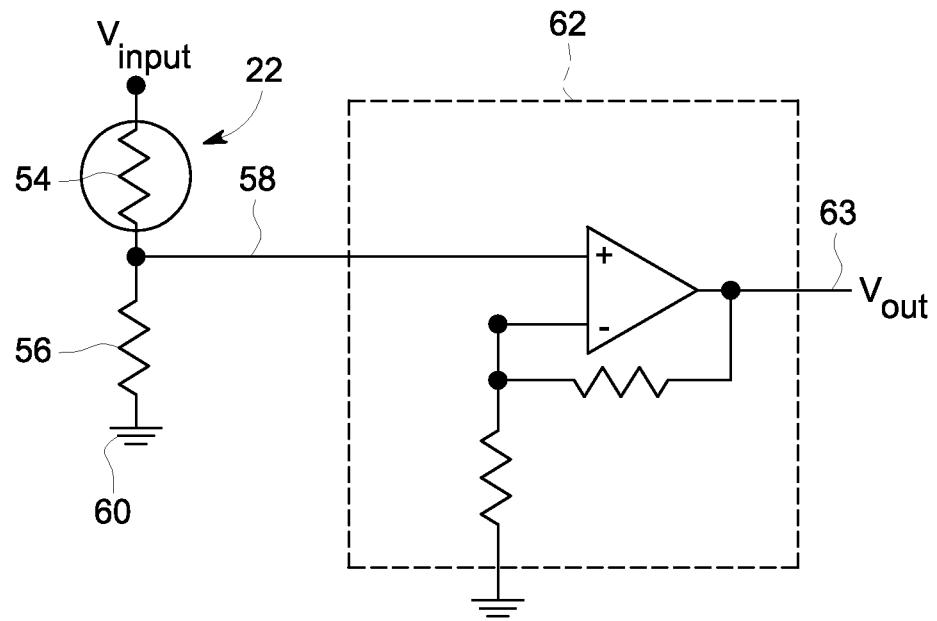
FIG. 5 illustrates one type of signal conditioning for an output signal from a variable resistive sensor, such as a temperature sensor.

FIG. 5 illustrates an exemplary embodiment of the temperature sensor 22 shown in FIG. 3. As illustrated in FIG. 5, the temperature sensor 22 includes a thermistor 54 that forms part of a voltage divider with another resistor 56. An output signal from the temperature sensor 22 is available along line 58. The output signal at line 58 is an absolute voltage signal that is measured between line 58 and ground 60. The thermistor 54 receives a drive signal ($V_{input}$) and generates an output signal on line 58 that varies based upon the value of the thermistor 54.

The output signal on line 58 is fed into an amplifier 62 such that an amplified output signal ($V_{out}$) is available at point 63.

Although two different types of sensors and amplifiers are illustrated in FIGS. 4 and 5, it should be understood that various different types of sensors and amplifiers could be utilized. The cardiac output sensor 24 shown in FIG. 3 is similar to the temperature sensor 22 in that the cardiac output sensor 24 includes a variable resistor that is formed as part of a voltage divider. The amplifier 62 shown in FIG. 5 could be used with the cardiac output sensor and the gain adjusted in a known manner.

Referring back to FIG. 3, each of the sensors 20, 22 and 24 communicates to an interface circuit 64 through one of the respective multi-mode input ports 38. The interface circuit 64 includes various configurable components, including an analog switching network and a variable voltage supply 15 that allows the interface circuit to both supply the desired drive signal to the connected sensors as well as to provide the output signal from the sensors to a detection module 66. The detection module 66 includes a plurality of individual amplifiers and conditioning circuits, such as the amplifiers 50 and 62 shown in FIGS. 4 and 5.

As indicated above, the interface circuit 64 includes a variable voltage supply 65 that can supply the required drive signal to the sensors connected to any one of the three input ports 38. The value of the voltage from the supply 65 is controlled by a processor included in the module 36.

When any one of the sensors is initially connected to one of the input ports, the voltage supply 65 contained within the interface circuit 64 generates a default voltage signal to the sensor. The default signal is a known, defined voltage that is applied to the sensor. Based upon the default signal applied to the sensor, the sensor generates an output signal that is received at the interface circuit 64. The output signal from the sensor then passes through a default amplifier contained within the detection module 66 and is received by the analog to digital converter 68. The analog to digital converter 68 converts the analog output signal to a digital output signal, which is received by the processor 70 that is included in the data acquisition module 36. Although the processor 70 is shown as a standalone component, it should be understood that the processor 70 could also be included within the detection module 66.

The processor 70 includes a memory 72 that includes a plurality of stored sensor profiles. The stored sensor profiles are pre-determined, representative responses that represent the anticipated output signal that should be received within the processor 70 upon the application of the default signal by the voltage source in the interface circuit 64 to the respective sensor connected to the input port 38. As an illustrative example, when the default signal is applied to the pressure sensor 20 shown in FIG. 4, the output signal received at the processor 70 will correspond to one of the sensor profiles. Based upon the comparison within the processor 70, the data acquisition module 36 can determine the type of sensor connected to the input port 38. The determined type of sensor is relayed to the patient monitor controller 12 through the communication line 74 as a sensor identifier. In addition, the digitized output signal from the sensor is conveyed to the patient monitor controller 12 through the output line 76. In this manner, the patient monitor controller 12 is able to receive the digitized output signal as well as an indication of the sensor type. Based upon this information, the patient monitor controller 12 can operate the display 14 to properly display the physiological data received from the patient.

The processor 70 further communicates to the detection module 66 and, through a series of switches and digital register settings, controls the amplifier that is connected to the sensor at each of the input ports 38. The specific amplifier is selected based upon the type of sensor connected to the input port. In addition, the processor 70 communicates to the interface circuit 64, which allows the processor 70 to control the voltage drive signal supplied to each of the sensors. Additionally, the interface circuit can be configured to receive the specific output signal from the sensor. As discussed previously, the pressure sensor 20 includes a differential output signal while the temperature sensor 22 and the cardiac output sensor 24 include an absolute voltage signal relative to ground.

Figure 6:
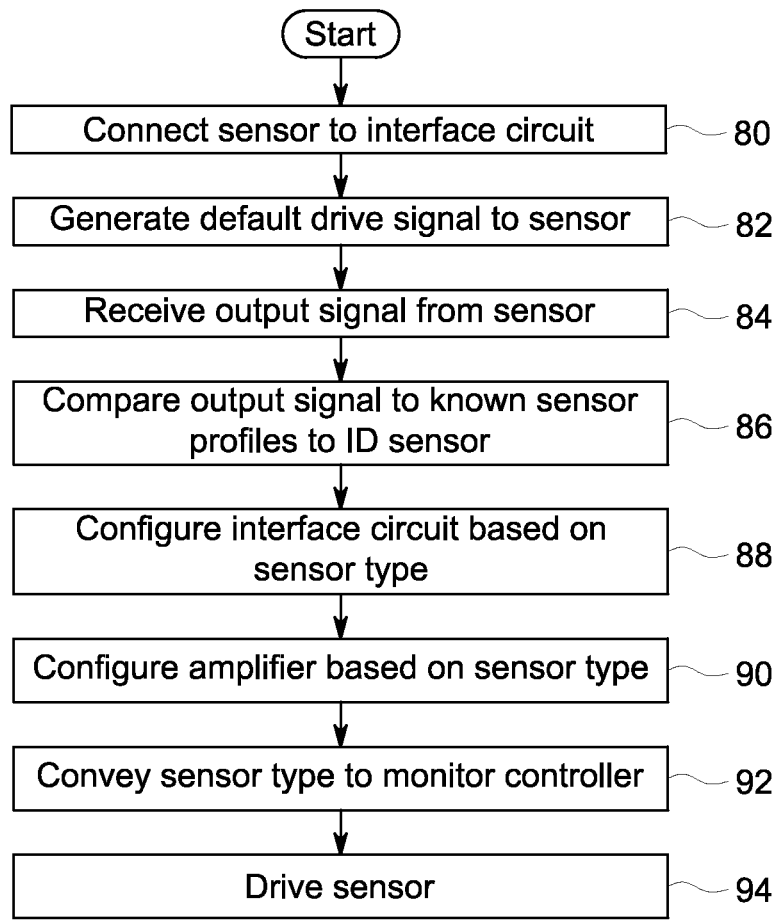
FIG. 6 is a flowchart illustrating the steps carried out by the system to determine the type of sensor.

FIG. 6 illustrates one example of the operational steps carried out by the system of the present disclosure to initially determine the type of sensor connected to the multi-mode input ports and, once the type of sensor is identified, provide the required drive signal to the sensor and connect the sensor to the required amplification circuit.

Initially, the sensor is connected to one of the multi-mode input ports, which in turn is connected to the interface circuit, as illustrated in step 80. Once the sensor is coupled to the interface circuit through the input port, the data acquisition module generates a default drive signal to the sensor, as indicated in step 82. As illustrated in FIG. 3, the processor 70 is in communication with the interface circuit 64 to indicate that the power supply 65 of the interface circuit 64 should generate the default drive signal, which is then received by the respective sensor 20, 22 or 24 connected to the input port 38. As described previously with respect to FIGS. 4 and 5, the default drive signal cause the sensor to generate an output signal which is received from the sensor in step 84. The output signal received from the sensor in step 84 is based upon the default drive signal sent to the sensor by the interface circuit 64. Since each of the individual sensors has different characteristics, the output signal received from the sensor is going to be dependent upon the physical characteristics of the sensor itself.

In step 86, the processor 70 compares the returned output signal to known sensor profiles that are maintained in a memory 72 of the processor 70. Once the type of sensor is identified, the processor 70 configures the interface circuit 64 to accept both the output signal from the sensor and to create the correct drive signal to the sensor, as illustrated in step 88. In addition to configuring the interface circuit, the processor 70 sends a signal to the detection circuit 66 which manipulates a series of switches to insure that the proper amplifier is coupled to receive the output signal from the sensor, as shown in step 90.

Once the drive signal and amplification circuit have been correctly coupled to the input port, the output signal from the sensor is fed through the analog to digital converter and ultimately received at the patient monitor controller. In addition to the amplified and digitized output signal, the processor 70 sends a sensor identifier to the patient monitor controller through the communication line 74, as indicated in step 92. Once the patient monitor controller receives both the sensor identifier and the output signal, the patient monitor controller can display the physiological data properly on the display unit 14. As indicated in step 94, the data acquisition module 36 continues to drive the sensor utilizing the identified proper drive signal.

As indicated above, the method and system of the present disclosure allows the patient monitor to include multiple input ports that can receive sensors of various different types. Once the sensor is attached to the patient monitor, the patient monitor identifies the sensor type and provides the required drive signal and conditioning circuit such that the output signal from the sensor is properly conditioned and supplied to the patient monitor controller. The multi-mode output port allows the patient monitor to include fewer output ports while still allowing for configuration with different types of sensors.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A data acquisition module for use with a patient monitor that receives and monitors physiological data generated as an output signal from one or more sensors of a plurality of different sensor types connected to a patient, comprising:

at least one multi-mode input port included in the module for communication with one of the sensors when the sensor is connected to the input port;

an interface circuit coupled to the input port, wherein the interface circuit includes an adjustable power supply that applies an analog drive voltage signal to the sensor based on the sensor type and is operable to selectively apply an analog default voltage signal to the sensor when the sensor is initially connected to the input port, wherein the analog default voltage signal is independent of the type of sensor; and a processor positioned to receive the output signal from the sensor in response to the analog default voltage signal, wherein the processor compares the output signal generated in response to the analog default voltage signal to known sensor profiles which are pre-determined anticipated responses upon application of the analog default voltage signal and determines the type of sensor connected to the input port based on the comparison to the known sensor profiles, wherein the analog drive voltage signal applied to the sensor has a value selected based upon the determined sensor type.

2. The module of claim 1 further comprising a detection module including a plurality of amplifiers, wherein the detection module routes the output signal from the sensor to one of the plurality of amplifiers to create an amplified output signal based upon the determined type of sensor connected to the input port.

3. The module of claim 1 wherein the sensor is selected from a group consisting of a pressure sensor and a temperature sensor.

4. The module of claim 2 further comprising an analog to digital converter operable to convert the amplified output signal to a digital output signal, wherein the processor receives the digital output signal and provides the digital output signal and a sensor identifier to the patient monitor.

5. The module of claim 1 wherein the interface circuit is configured to receive both a differential output signal and an output signal relative to ground.

6. A method of identifying a sensor connected to a multi-function input port of a patient monitor, the sensor generating an output signal indicative of a physiological parameter of a patient, comprising:

connecting the sensor to the multi-function input port;

generating an analog default voltage signal to the sensor from an adjustable power supply included in an interface circuit when the senor is initially connected to the input port, wherein the analog default voltage signal is independent of the type of sensor;

receiving the output signal from the sensor generated in response to the analog default voltage signal;

comparing the output signal generated in response to the analog default voltage signal to known sensor profiles;

identifying the type of sensor connected to the input port based upon the comparison of the output signal generated in response to the analog default voltage signal to the known sensor profiles stored in a memory of a processor; and operating the adjustable power supply to apply an analog drive voltage signal to the sensor having a value based on the identified type of sensor.

7. The method of claim 6 further comprising the step of connecting the output signal from the sensor to one of a plurality of amplifiers based upon the identified type of sensor to generate an amplified output signal.

8. The method of claim 7 further comprising the steps of:

converting the amplified output signal to a digital output signal; and providing the digital output signal and a sensor identifier to the patient monitor.

9. The method of claim 6 wherein the interface circuit is configured to receive both a differential signal and a signal relative to ground.

10. A patient monitor that receives physiological data generated as an output signal from one or more sensors connected to a patient, comprising:

a data acquisition device operable to receive the output signals from the sensors and condition the output signals and identify a type of sensor, the data acquisition module comprising:

at least one multi-mode input port formed in the data acquisition module for communication with one of the sensors when the sensor is connected to the input port;

an interface circuit coupled to the input port, wherein the interface circuit includes an adjustable power supply that applies an analog drive voltage signal to the sensor and is operable to selectively apply an analog default voltage signal to the sensor when the sensor is initially connected to the input port, wherein the analog default voltage signal is independent of the type of sensor; and a processor positioned to receive the output signal from the sensor, wherein the processor compares the output signal to known sensor profiles which are pre-determined anticipated responses upon application of the analog default voltage signal and determines the type of sensor connected to the input port based on the comparison to the known sensor profiles, wherein the processor generates a sensor identifier;

a patient monitor controller positioned to receive the output signal and the sensor identifier, wherein the patient monitor controller interprets the output signal based upon the sensor identifier and displays the conditioned output data.

11. The patient monitor of claim 10 further comprising a detection module including a plurality of amplifiers, wherein the detection module routes the output signal from the sensor to one of the plurality of amplifiers to create an amplified output signal based upon the determined type of sensor connected to the input port.

12. The patient monitor of claim 10 wherein the analog drive voltage signal has a value selected based upon the identified type of the sensor.

13. The patient monitor of claim 11 further comprising:

an analog to digital converter operable to convert the amplified output signal to a digital output signal, wherein the processor receives the digital output signal and provide the digital output signal and a sensor identifier to the patient monitor.

14. The patient monitor of claim 12 wherein the adjustable power supply is operable to provide the analog default voltage signal and the analog drive voltage signal.

15. The patient monitor of claim 10 wherein the interface circuit is configured to receive both a differential output signal and an output signal relative to ground.

* * * * *